US010473596B2

(12) United States Patent
Kambe

(10) Patent No.: US 10,473,596 B2
(45) Date of Patent: Nov. 12, 2019

(54) X-RAY INSPECTION APPARATUS

(71) Applicant: Shimadzu Corporation, Kyoto (JP)

(72) Inventor: Goro Kambe, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 93 days.

(21) Appl. No.: 15/899,495

(22) Filed: Feb. 20, 2018

(65) Prior Publication Data

US 2018/0252656 A1 Sep. 6, 2018

(30) Foreign Application Priority Data

Mar. 6, 2017 (JP) .................. 2017-041666

(51) Int. Cl.
*G01N 23/04* (2018.01)
*G01N 23/083* (2018.01)

(52) U.S. Cl.
CPC ......... *G01N 23/043* (2013.01); *G01N 23/083* (2013.01); *G01N 2223/3307* (2013.01); *G01N 2223/6113* (2013.01); *G01N 2223/6116* (2013.01)

(58) Field of Classification Search
CPC ......... G01N 23/043; G01N 2223/3307; G01N 2223/6113; G01N 2223/6116; G01N 23/083
See application file for complete search history.

(56) References Cited

U.S. PATENT DOCUMENTS 8,275,093 B2 * 9/2012 Rothschild ........... G01V 5/0016
378/53
2010/0239069 A1 * 9/2010 Bourdeaux .............. A61B 6/00
378/96

FOREIGN PATENT DOCUMENTS

JP 2002-350367 A 12/2002
JP 2011-179936 A 9/2011

OTHER PUBLICATIONS

Extended European Search Report dated Aug. 2, 2018 in corresponding European Application No. 18157902.0; 8 pages.
David Bernard et al., "Considerations for Minimizing Radiation Doses to Components during X-Ray Inspection", IEEE/CPMT/SEMI STS: Int'l Electronics Manufacturing Technology Symposium, Jul. 16, 2003, pp. 369-377.

* cited by examiner

*Primary Examiner* — Kiho Kim
(74) *Attorney, Agent, or Firm* — Maier & Maier, PLLC

(57) ABSTRACT

An X-ray inspection apparatus includes an X-ray source, an X-ray detector, and a stage. A dose rate calculation unit of a control section calculates a dose rate at any position in an inspection space, a stage face information storage unit 32 stores stage face information, an irradiation history monitoring unit monitors a movement locus, a stage face cumulative irradiation dose calculation unit calculates cumulative irradiation dose distribution data, a stage face imaging range calculation unit calculates a stage face imaging range of the X-ray detector, and a dose distribution image display control unit extracts the cumulative irradiation dose distribution data in an imaging range and displays an image thereof.

3 Claims, 4 Drawing Sheets

X-RAY INSPECTION APPARATUS

TECHNICAL

The present invention relates to an X-ray inspection apparatus for industrial applications, and particularly to an X-ray inspection apparatus suitable for inspection of internal defects of a semiconductor product and the like.

BACKGROUND

An X-ray inspection apparatus is widely used for nondestructive inspection of a semiconductor product and the like. For example, in inspection of the presence or absence of internal defects of a semiconductor component such as an integrated circuit (IC) mounted on a printed board, an inspection target is irradiated with X-rays such that an X-ray fluoroscopic image is captured, and the quality of a product is determined on the basis of the X-ray fluoroscopic image.

In a case where an inspection target is small, such as a semiconductor product on a printed board, it is desirable to perform inspection by capturing an enlarged X-ray fluoroscopic image. Therefore, inspection is performed by using an apparatus in which a two-dimensional X-ray detector is disposed to face an X-ray generation device irradiating a cone beam-shaped X-ray, an XYZ stage which is movable in a three-dimensional direction is disposed in an inspection space therebetween, an inspection target object is placed thereon, an observation position is defined by moving the placed inspection target object in XY directions, and an observation region can be enlarged and reduced by moving the inspection target object in a Z direction.

However, since radiation resistance design is not applied to a general semiconductor component, there is a case where electrical characteristics are changed due to the influence of X-rays applied during X-ray inspection, and thus the semiconductor component is damaged.

Since it is known that such a problem depends on a cumulative irradiation dose of X-rays applied to an inspection target object, a cumulative irradiation dose value of X-rays applied to an inspection target object is managed through expectation or measurement.

For example, in an X-ray inspection apparatus provided and used in a mounting assembly line for a printed board, in a case where a plurality of semiconductor components are placed to be dotted at positions separated from each other on a printed board, a method may be used in which an X-ray irradiation region for the printed board is divided into small regions, and imaging is performed a plurality of number of times while allowing irradiation regions to partially overlap each other. In this inspection, an X-ray irradiation scheduled dose value per component is calculated on the basis of position data of a mounting component and an X-ray irradiation dose value for each X-ray irradiation region, and is not made to exceed an X-ray irradiation allowable dose value through comparison with the X-ray irradiation allowable dose value per component (refer to JP-A-2002-350367).

A method is disclosed in which a printed board is placed on an observation table of an X-ray inspection apparatus, a position and a height of a stage are adjusted such that a position of an inspection target object is located between an X-ray source and an X-ray detector, and a cumulative irradiation dose of X-rays in the inspection target object is managed in the following method (refer to JP-A-2011-179936).

In other words, prior to inspection, reference X-ray conditions (a tube current, a tube voltage, a distance from the X-ray source to the observation table (hereinafter, referred to as an "SOD")) are set in advance, and a dosimeter is disposed on the observation table so as to measure a dose rate which is then stored in a control section. During inspection, an inspection target object is placed on the observation table, the observation table is moved, X-rays are applied at a desired position, and an X-ray fluoroscopic image is captured and is displayed on a display. Next, X-ray conditions (a tube current, a tube voltage, and an SOD) during X-ray irradiation are recorded, and an irradiation time is measured, and a dose rate in these X-ray conditions is calculated on the basis of a dose rate under the reference conditions stored in advance.

Specifically, since it is known that a dose rate is proportional to the square of a tube voltage, proportional to a tube current, and inversely proportional to the square of an SOD, the dose rate is calculated on the basis of a dose rate under the reference conditions by using set conditions of a tube voltage, a tube current, and an SOD. A product between the irradiation time and the dose rate until the X-ray conditions are changed is calculated, and thus an irradiation dose in the inspection target object is obtained. The same computation is performed under changed X-ray conditions whenever the X-ray conditions are changed for the same inspection target object, and an irradiation dose is added, so that a cumulative irradiation dose from starting of X-ray irradiation is computed (refer to JP-A-2011-179936).

SUMMARY

In the above-described related art, the former related art is based on mounting component data including an attachment position of a mounting component on a printed board being acquired, and is thus useful in a case where such mounting component data is prepared, and the same printed board in an assembly line or the like is inspected under the same X-ray fluoroscopic image capturing conditions, but cannot be applied in a case where mounting component data is not prepared.

On the other hand, in the latter related art, mounting component data for an inspection target object is not necessary, a position (including a height) of a semiconductor component on a printed board is directly adjusted by moving the observation stage, and then observation is performed.

In this case, the observation stage is freely moved in three-dimensional (XYZ) directions until an optimal imaging position is found in a state in which X-rays are applied, and then a fluoroscopic image is captured at an optimal position. Therefore, in a case where there are a plurality of semiconductor components on a printed board, an optimal imaging position for each semiconductor component is found, and imaging is performed at the position.

In the end, a cumulative irradiation dose on the observation stage until observation is finished from a time point of starting X-ray irradiation is defined depending on a movement locus until an optimal position is found. In this case, cumulative irradiation doses at respective positions on the printed board are different from each other. Therefore, even if a cumulative irradiation dose at a certain point is calculated, in a case where inspection is performed at a plurality of observation positions, it is hard to accurately recognize an irradiation dose at each position.

A small semiconductor component is problematic in terms of a cumulative irradiation dose applied in the small area thereof, but irradiation doses may be greatly different from each other at a position of an inspection target semiconductor component and a position in the vicinity thereof depending on a movement locus of the stage when an observation position is changed, and thus it is desirable to be able to two-dimensionally recognize an irradiation dose at each position on a printed board. It is also desirable to recognize an irradiation dose distribution of the inside of an observation target semiconductor component.

Therefore, an object of the present invention is to provide an X-ray inspection apparatus which can recognize a cumulative irradiation dose applied to an inspection target object as a two-dimensional distribution image with respect to the inspection target object such as a semiconductor component placed on a stage.

Another object of the present invention is to be able to recognize a cumulative irradiation dose in an inspection target object placed at any position on a stage.

Still another object of the present invention is to be able to display a cumulative irradiation dose distribution image which is enlarged in an equivalent manner to an X-ray fluoroscopic image so as to correspond to an imaging region of the X-ray fluoroscopic image although an enlarged X-ray fluoroscopic image of an inspection target object is frequently captured in X-ray inspection of a small component.

Solution to Problem

In order to solve the above-described problem, according to an aspect of the present invention, there is provided an X-ray inspection apparatus including an X-ray source; an X-ray detector that is disposed to face the X-ray source with an inspection space interposed therebetween; a stage that is movable to any position in the inspection space by a three-dimensional movement mechanism; a dose rate calculation unit that obtains a reference dose rate for at least one position in the inspection space under a tube current and a tube voltage used as references, and stores the reference dose rate as "reference dose rate data" in advance, and calculates a dose rate at any position in the inspection space as "inspection space dose rate data" on the basis of the "reference dose rate data" by setting a tube current and a tube voltage used for inspection of an inspection target object; a stage face information storage unit that stores "stage face information" including a stage reference point defined for the stage and relative position information for defining a range of a stage face; an irradiation history monitoring unit that monitors a movement locus of the stage reference point at each time point from starting of X-ray irradiation to ending of X-ray irradiation, and stores the movement locus as "irradiation history information"; a stage face cumulative irradiation dose calculation unit that calculates a cumulative irradiation dose at each position on the stage face of the stage on the basis of the "irradiation history information", the "stage face information", and the "inspection space dose rate data", and stores the cumulative irradiation dose as "cumulative irradiation dose distribution data"; a stage face imaging range calculation unit that calculates "stage face imaging range data" indicating a range of the stage face imaged by the X-ray detector at a position where an X-ray fluoroscopic image of the inspection target object is captured; and a dose distribution image display control unit that extracts cumulative irradiation dose distribution data for a region corresponding to the "stage face imaging range data" from the "cumulative irradiation dose distribution data" as "imaging range cumulative dose distribution data", and displays an image of the imaging range cumulative dose distribution data on the display device, in which a position of the stage is adjusted such that an observation region of the inspection target object placed on the stage face of the stage is located on an X-ray optical axis connecting the X-ray source to the X-ray detector, and then an X-ray fluoroscopic image of the inspection target object is captured and is displayed on a display device.

According to the aspect of the present invention, if a tube current and a tube voltage of the X-ray source used for inspection are set when X-ray inspection of an inspection target object is performed, the dose rate calculation unit can calculate a dose rate at each position in the inspection space on the basis of the "reference dose rate data" stored in advance prior to the inspection, and thus a dose rate at a desired position is calculated as the "inspection space dose rate data" when necessary.

In a case where inspection is started in a state in which an inspection target object is placed on the stage face, the irradiation history monitoring unit stores a movement locus of the stage reference point at each time point from starting of X-ray irradiation to ending thereof as the "irradiation history information".

The stage face cumulative irradiation dose calculation unit calculates cumulative irradiation dose at each position on the stage face on the basis of the "irradiation history information", the "stage face information", and the "inspection space dose rate data". Consequently, the "cumulative irradiation dose distribution data" at each position on the stage face is acquired.

The stage face imaging range calculation unit calculates the "stage face imaging range data" indicating a range of the stage face imaged by the X-ray detector at that time at a position where an X-ray fluoroscopic image of the inspection target object is captured. This is obtained on the basis of geometric positional relationships among the "stage face information" at the position where the X-ray fluoroscopic image is captured, the X-ray source, and the X-ray detector.

If the "stage face imaging range data" is calculated, the dose distribution image display control unit extracts cumulative irradiation dose distribution data for a partial region corresponding to the "stage face imaging range data" from the "cumulative irradiation dose distribution data" which is distribution data for the entire stage face as the "imaging range cumulative dose distribution data", generates an image thereof, and displays the image on the display device as a two-dimensional distribution image of the cumulative irradiation dose.

According to the present invention, a cumulative irradiation dose in a region corresponding to a captured X-ray fluoroscopic image can be visually recognized from a two-dimensional distribution image.

A cumulative irradiation dose applied during X-ray inspection can be recognized in the unit of a component to be inspected.

According to the present invention, it is possible to recognize a two-dimensional distribution image of a cumulative irradiation dose in the same region as that of an X-ray fluoroscopic image in accordance with an imaging region in which the X-ray fluoroscopic image is captured without particularly being aware of a placement position on a stage and without being influenced by enlargement or reduction of the X-ray fluoroscopic image.

In the aspect of the invention, the dose rate calculation unit may move the stage under the tube current and the tube voltage used as references, measure a dose per unit time at a plurality of positions in the inspection space with a dosimeter placed on the stage face, store the dose as a "reference dose rate table", and calculate the "inspection space dose rate data" at any position in the inspection space on the basis of the "reference dose rate table".

Consequently, it is possible to increase the accuracy of "inspection space dose rate data" calculated for any position in the inspection space.

In the aspect of the invention, the dose distribution image display control unit may display the captured X-ray fluoroscopic image of the inspection target object and a two-dimensional distribution image of a cumulative irradiation dose based on the "imaging range cumulative dose distribution data" corresponding to the X-ray fluoroscopic image to be arranged side by side or to be superimposed on each other.

Consequently, an X-ray fluoroscopic image and a two-dimensional distribution image of a cumulative irradiation dose can be observed through comparison, and thus the influence of and a fault caused by X-ray irradiation can be visually checked.

DETAILED DESCRIPTION OF THE FIGURES

Figure 1:
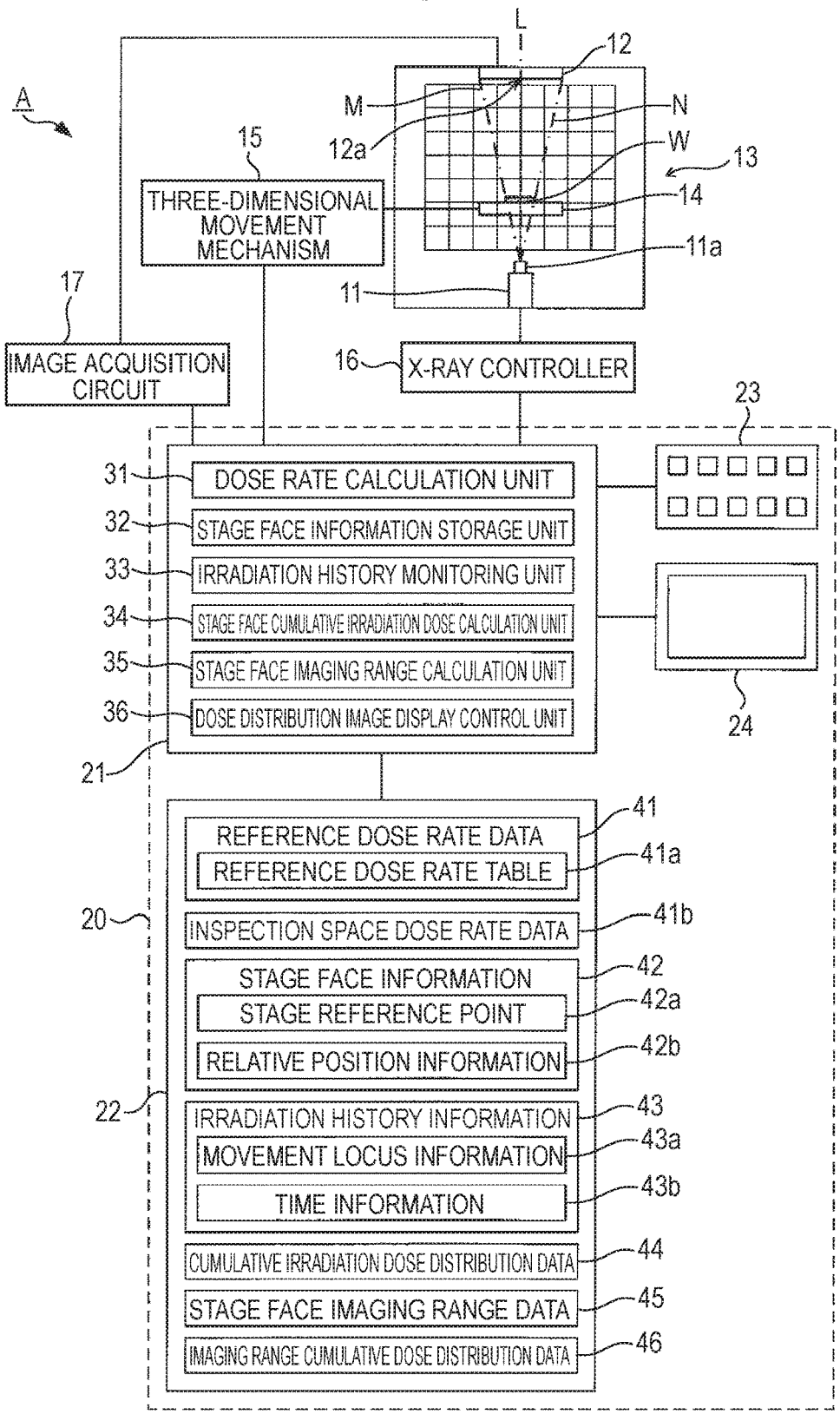
FIG. 1 is a block diagram illustrating a configuration of an X-ray inspection apparatus according to an embodiment of the present invention.

Hereinafter, an embodiment of the present invention will be described with reference to the drawings. FIG. 1 is a block diagram schematically illustrating a configuration of an X-ray inspection apparatus A according to an embodiment of the present invention.

A micro-focus X-ray tube is used for an X-ray generation device 11 which is an X-ray source. An irradiation central point 11a formed in the micro-focus X-ray tube is a dotted X-ray generation point, and irradiates a cone beam-shaped X-ray vertically upward. A two-dimensional X-ray detector 12 is disposed to face the X-ray generation device 11 over the X-ray generation device 11, and a stage 14 on which an inspection target object W is placed is disposed in an inspection space 13 therebetween in a state in which a placement face (stage face) is horizontal. The X-ray detector 12 is disposed such that an X-ray optical axis L connecting the irradiation central point 11a of the X-ray generation device 11 to a light reception face central point 12a of the X-ray detector 12 is a vertical line. The stage 14 is formed of a square plate (for example, an aluminum plate) through which an X-ray is transmitted, and is movable to any position in the inspection space 13 by a three-dimensional movement mechanism 15. An XYZ coordinate system is defined in the inspection space 13, and any position can be specified by XYZ coordinates. The inspection space 13 is surrounded by an X-ray protection box for safety.

A control section 20 is formed of computer hardware including a microprocessor (CPU) 21, memory (a ROM, a RAM, or an HDD) 22, an input device (a mouse, a joystick, or a keyboard) 23, and a display device (liquid crystal panel) 24, and controls the X-ray generation device 11, the X-ray detector 12, and the three-dimensional movement mechanism 15.

In a case where set values of a tube current and a tube voltage or an activation/stoppage command is input, the control section 20 sends a control signal to an X-ray controller 16. The X-ray generation device 11 sets a tube current and a tube voltage therein in response to the control signal from the X-ray controller 16, and controls irradiation starting or irradiation stopping.

A detection signal for an X-ray fluoroscopic image is sent from the X-ray detector 12 to an image acquisition circuit 17 such that an image signal is formed, and the image signal is sent to the control section 20 so as to be displayed on the display device 24.

The three-dimensional movement mechanism 15 moves a position of the stage 14 to any position in a case where a position control signal is input from the control section 20. The control section 20 stores the XYZ coordinate system of the inspection space 13, and also stores a position coordinate of the irradiation central point 11a of the X-ray generation device 11, a position coordinate of the light reception face central point 12a of the X-ray detector 12, and an origin position as a reference position for specifying a position of the stage 14. Therefore, if the stage 14 is returned to the origin by the three-dimensional movement mechanism 15 so as to be initialized, and is then moved from the origin position, the current position coordinate of the stage 14 can be subsequently recognized on the basis of a movement amount, and positional relationships with the X-ray generation device 11 and the X-ray detector 12 can also be recognized.

A control program which is computer software for realizing each function executed in the present invention is installed in the control section 20. When operations performed by the control section 20 are described as functional blocks, the control section 20 includes a dose rate calculation unit 31, a stage face information storage unit 32, an irradiation history monitoring unit 33, a stage face cumulative irradiation dose calculation unit 34, a stage face imaging range calculation unit 35, and a dose distribution image display control unit 36.

The dose rate calculation unit 31 actually measures a dose rate (a dose rate per unit time) at a single position in the inspection space 13 by using a dosimeter before the inspection target object W is inspected in, for example, periodic inspection, and stores the dose rate as reference dose rate data 41. As described above, it is known that a dose rate is proportional to the square of a tube voltage, proportional to a tube current, and inversely proportional to the square of a distance. Therefore, a dose per unit time is actually measured for a single point with any position coordinate in the inspection space 13 under a tube current and a tube voltage used as references, and thus a dose rate for any point in the inspection space 13 can also be theoretically calculated since a position coordinate of the irradiation central point 11a of the X-ray generation device 11 is defined, and a distance from the irradiation central point 11a to the actually measured point can be known. Therefore, even in a case where a tube current or a tube voltage is changed, a dose rate can be theoretically calculated.

In order to increase computation accuracy of a dose rate distribution state in the inspection space 13, a dosimeter may be placed on the stage 14 and be moved such that dose rates are actually measured at a plurality of (multiple) points, and a reference dose rate table 41a (a table of reference dose rate data at a plurality of points) of the inspection space 13 may be created and used. Dose rates may be actually measured after tube voltages or tube currents are set to a plurality of values, and may be obtained through interpolation computation or theoretic computation with respect to tube voltages or tube currents therebetween.

A dose rate is technically hard to be actually measured in a space close to the X-ray generation device 11, and may thus be obtained through theoretic computation on the basis of a plurality of actually measured values at positions separated from the X-ray generation device 11.

Since the tube current and the tube voltage used during inspection of the inspection target object W are set, the dose rate calculation unit 31 calculates a dose rate at any position in the inspection space 13 as inspection space dose rate data 41b by using the reference dose rate data 41 (reference dose rate table 41a) as necessary. The calculated inspection space dose rate data 41b at any position is used for computation of a cumulative irradiation dose which will be described later.

The stage face information storage unit 32 stores stage face information 42 including a stage reference point 42a defined for the stage 14, and relative position information 42b for defining a range of a stage face with a position of the stage reference point 42a as a reference.

The stage reference point 42a is a single point defined on the stage face of the stage 14, and is monitored as a representative point of the stage face such that a position of the stage 14 in the inspection space 13 can be recognized, and thus a movement locus of the stage 14 can be tracked.

The relative position information 42b is information regarding a relative position for defining a range of the stage face for the stage reference point 42a, and a position coordinate of each point included in the stage face of the stage 14 can be specified in combination with the stage reference point 42a.

A location on the stage 14 to which the stage reference point 42a is set is not particularly limited, but, in the present embodiment, since the stage 14 having the planar square stage face is used, and a range of the stage face can be specified by setting the stage reference point 42a as a central point of the square and using the relative position information 42b as the stage face information 42 in which four points of four corners of the square shape are set as a range.

The irradiation history monitoring unit 33 monitors a movement locus of the stage reference point 42a at each time point from starting of X-ray irradiation to ending of X-ray irradiation, and stores the movement locus as irradiation history information 43. Movement locus information 43a (position coordinate information X, Y and Z) which is a path along which the stage reference point 42a is moved, and time information 43b (time coordinate information T) at each point on a movement locus are stored in the irradiation history information 43 in correlation with each other (for example, four-dimensional coordinate data of X, Y, Z, and T).

The monitoring is continuously performed from an irradiation starting time point of an X-ray to an irradiation ending time point. The monitoring is performed not only in a period in which an X-ray fluoroscopic image is captured at a desired observation position but also in a period in which the stage 14 is being moved or a period in which an X-ray is continuously applied after observation is completed, and thus the monitoring is performed in the entire period in which an X-ray is actually applied.

The stage face cumulative irradiation dose calculation unit 34 calculates a cumulative irradiation dose at each position on the stage face of the stage 14 on the basis of the irradiation history information 43 (the movement locus information 43a and the time information 43b), the stage face information 42 (the stage reference point 42a and the relative position information 42b), and the inspection space dose rate data 41b, and stores the cumulative irradiation dose as cumulative irradiation dose distribution data 44.

Specifically, first, with respect to the stage reference point 42a, each point on a movement locus of the stage reference point 42a is extracted from the movement locus information 43a, and the inspection space dose rate data 41b for each point on the movement locus is calculated. A product between the inspection space dose rate data 41b and the time information 43b is obtained for each point on the movement locus, and thus an irradiation dose for each point on the movement locus is obtained. Irradiation doses at the respective points on the movement locus are added together, and thus a cumulative irradiation dose for the stage reference point 42a can be obtained.

The same calculation is performed on respective points on the entire stage face other than the stage reference point 42a of the stage 14 by using the relative position information 42b along with the stage reference point 42a such that a cumulative irradiation dose can be calculated, and thus a calculation result for the entire stage face of the stage 14 is stored as the cumulative irradiation dose distribution data 44. The cumulative irradiation dose distribution data 44 may be held as data, and an image thereof is not necessarily displayed on the display device 24 during inspection of the inspection target object W, but, in a case where the image is displayed, a cumulative irradiation dose distribution for the entire stage face of the stage 14 can be observed (refer to FIGS. 4 and 7 which will be described later).

The cumulative irradiation dose distribution data 44 is continuously updated every moment as long as an X-ray is continuously applied, but may be updated by calculating a cumulative irradiation dose at a predetermined interval of, for example, 10 seconds to five minutes in order to suppress a processing amount in computation.

The stage face imaging range calculation unit 35 calculates stage face imaging range data 45 indicating a range of the stage face imaged by the X-ray detector 12 at a position where an X-ray fluoroscopic image of the inspection target object W is captured.

For example, in X-ray inspection in a case where the inspection target object W is small, it is preferable that an X-ray fluoroscopic image in which a region desired to be inspected is enlarged is captured, and inspection is performed. Thus, an imaging region is often not the entire stage face of the stage 14 but a part thereof. Therefore, if a range of the stage face corresponding to an imaging region is specified, and a cumulative irradiation dose in the range of the stage face is obtained, an irradiation dose in the imaging region can be recognized in detail, and thus it is necessary to specify a range of the stage face corresponding to an imaging range of an X-ray fluoroscopic image.

This range of the stage face may be defined through geometric computation by using the fact that a central point (a central point of an imaging region) on a captured X-ray fluoroscopic image is a point on the X-ray optical axis L connecting the irradiation central point 11a of the X-ray generation device 11 to the light reception face central point 12a of the X-ray detector 12, and a three-dimensional position coordinate of the stage face on the X-ray optical axis L during imaging is determined on the basis of position information from the three-dimensional movement mechanism 15.

In other words, as illustrated in FIG. 1, since a range of the stage face interposed between line segments M and N connecting the irradiation central point 11a to both ends of the light reception face of the X-ray detector 12 is a range of the stage face corresponding to an X-ray fluoroscopic image, the stage face imaging range data 45 can be calculated by geometrically calculating the range of the stage face interposed between the line segments M and N.

The dose distribution image display control unit 36 performs control of extracting cumulative irradiation dose distribution data for a region corresponding to the stage face imaging range data 45 from the cumulative irradiation dose distribution data 44 for the entire stage face of the stage 14 as imaging range cumulative dose distribution data 46, and displaying an image thereof on the display device 24. The displayed image is a dose distribution image of a region corresponding to an imaging region of an X-ray fluoroscopic image. Therefore, when images are displayed, the dose distribution image display control unit 36 performs control such that an X-ray fluoroscopic image and a dose distribution image are displayed in parallel to each other, or one thereof is displayed colored, and the dose distribution image and the X-ray fluoroscopic image are displayed to be superimposed on each other, and thus the images can be displayed to be easily recognized.

(Inspection Procedures)

Figure 2:
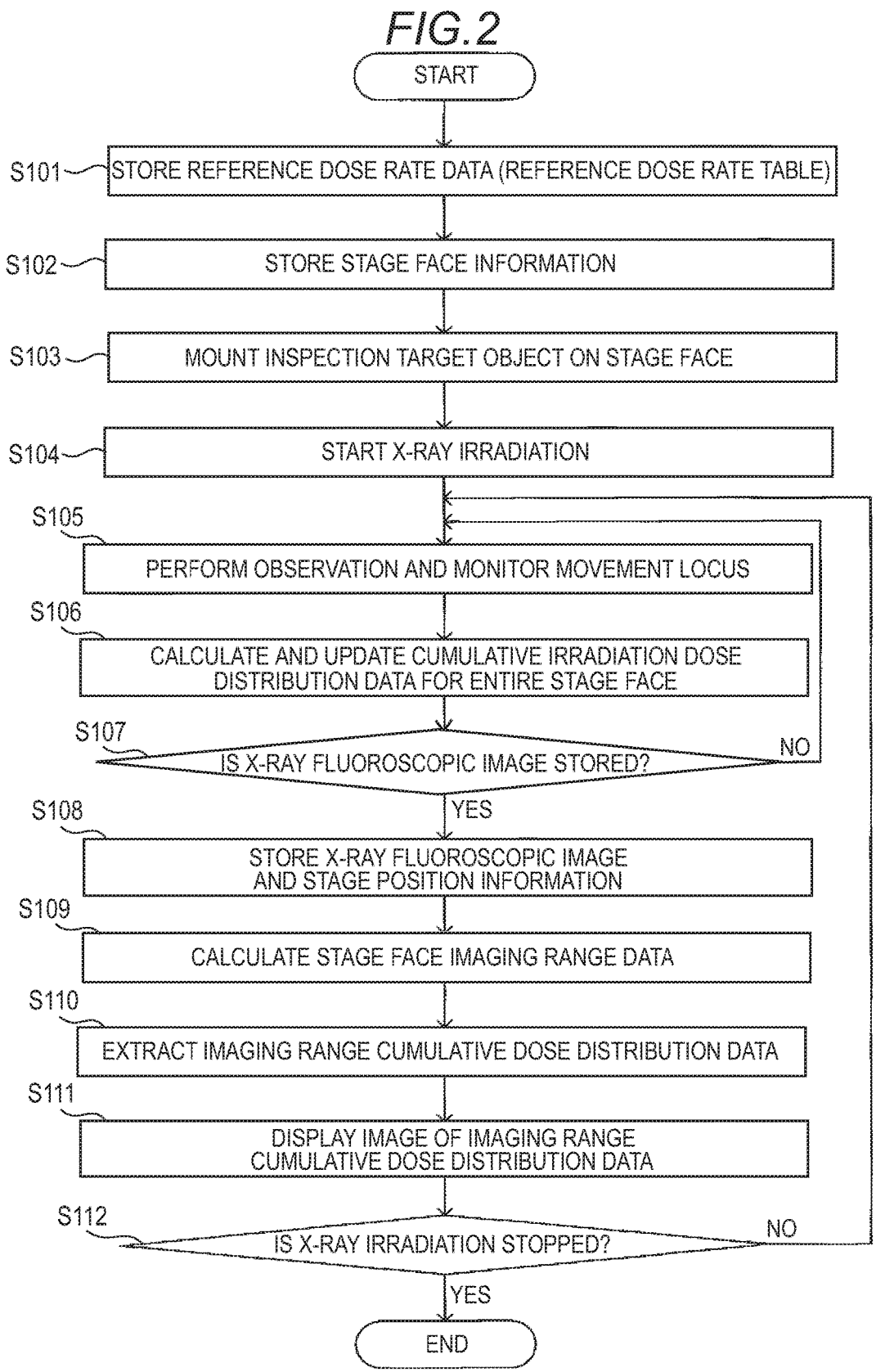
FIG. 2 is a flowchart illustrating examples of inspection procedures performed by the X-ray inspection apparatus of the present invention.
Figure 3:
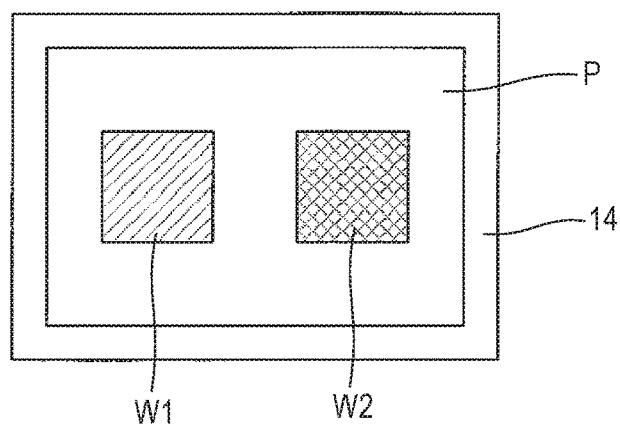
FIG. 3 is a diagram illustrating a state in which an inspection target printed board is placed on a stage.

Next, a description will be made of examples of inspection procedures performed by the X-ray inspection apparatus A with reference to a flowchart of FIG. 2. Herein, as illustrated in FIG. 3, the description will be made assuming that a printed board P on which two semiconductor components such as inspection target objects W (W1 and W2) are mounted is placed on the stage 14, the semiconductor component W1 is first inspected, and then the semiconductor component W2 is inspected.

In S101, prior to inspection of the semiconductor components W, the reference dose rate data 41 which is required to determine a dose rate of each point in the inspection space 13 is stored in advance. Specifically, a reference tube voltage and a reference tube current are set, an X-ray is applied from the X-ray generation device 11, a dosimeter is mounted on the stage 14 and is moved in the inspection space 13, and dose rates are measured at measurement points selected in a lattice shape so as to be stored as the reference dose rate table 41a. Thereafter, a dose rate of any point in the inspection space 13 is obtained through interpolation computation or theoretic computation by using the reference dose rate table 41a, and is used as the inspection space dose rate data 41b.

In S102, prior to inspection of the semiconductor components W, the stage reference point 42a and the relative position information 42b of the stage face are stored as the stage face information 42. If this information is stored, a position coordinate of each point of the stage face when the stage 14 is moved in the inspection space 13 can be specified through monitoring of the stage reference point 42a.

In S103, the printed board P is placed on the stage face of the stage 14.

In S104, an X-ray starts to be applied. The irradiation history information 43 starts to be monitored from this time point.

In S105, execution of observation of the inspection target object W (at first, W1) using X-ray irradiation and monitoring of a movement locus are continuously performed, and a movement locus (movement locus information 43a) of the stage reference point 42a at each time point (time information 43b) is stored as the irradiation history information 43.

In S106, the cumulative irradiation dose distribution data 44 of each point of the entire stage face is calculated and is also updated.

In S107, the presence or absence of a storage command for storing the current X-ray fluoroscopic image is checked, and, in a case where there is no storage command, the flow returns to S105, and thus execution of observation and monitoring of a movement locus are continuously performed.

In a case where there is input of the storage command, the flow proceeds to S108.

In S108, an X-ray fluoroscopic image is stored, and position information (that is, movement locus information of when the image is stored) of the stage face of the stage at that time is stored.

In S109, the stage face imaging range data 45 corresponding to a region in which the X-ray fluoroscopic image is captured is calculated on the basis of a geometric relationship (a positional relationship among the X-ray source, the X-ray detector, and the stage face).

In S110, the imaging range cumulative dose distribution data 46 which is dose distribution data in the region corresponding to the stage face imaging range data is extracted from the cumulative irradiation dose distribution data 44 which is dose distribution data of each point of the entire stage face.

In S111, an image of the extracted imaging range cumulative dose distribution data 46 is displayed.

In S112, the presence or absence of a stoppage command of X-ray irradiation is checked, and, in a case where there is no stoppage command, the flow returns to S105, and thus execution of observation of another inspection target object W (at second, W2) and monitoring of a movement locus are continuously performed.

On the other hand, in a case where there is input of the stoppage command of X-ray irradiation, irradiation is finished, observation is finished, and monitoring of the irradiation history information 43 is also finished.

In the above-described way, the same process is repeatedly performed until inspection of all inspection target objects W is completed.

Next, a description will be made of changes in cumulative irradiation dose distribution images obtained at two different time points in a case where inspection is performed according to the procedures described in FIG. 2.

Figure 4:
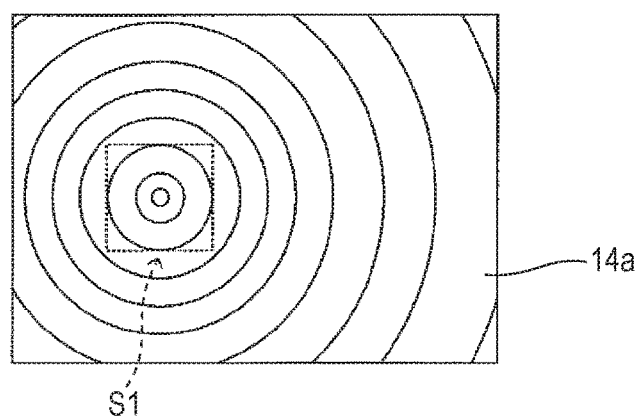
FIG. 4 is a schematic diagram illustrating cumulative irradiation dose distribution data of a first inspection target object.

FIG. 4 is a schematic diagram illustrating a display image 14a obtained in a case where cumulative irradiation dose distribution data for the entire stage 14 is calculated, and an image thereof is displayed right after an enlarged X-ray fluoroscopic image of the semiconductor component W1 is captured in inspection of the first semiconductor component W1.

Herein, for convenience of clarifying a temporal change of a cumulative irradiation dose distribution image, from the viewpoint of efficiently inspecting the first semiconductor component W1, the semiconductor component W1 is present on the X-ray optical axis L of the X-ray inspection apparatus A in a case where the printed board P is placed on the stage 14 such that adjustment in the XY directions is omitted. Next, an X-ray is applied to the semiconductor component W1, a position (magnification ratio) thereof in the Z direction is adjusted, observation is performed for the time being, and an image of the cumulative irradiation dose distribution data 44 for the entire stage 14 right after an X-ray fluoroscopic image of the semiconductor component W1 is captured is displayed. The display image 14a of the cumulative irradiation dose distribution data 44 obtained at this time point shows a substantially concentric cumulative irradiation dose distribution with the position of the X-ray optical axis L as the center (since the stage is not moved in the XY directions).

Figure 5A:
FIG. 5a is a schematic diagram illustrating an X-ray fluoroscopic image in a case where the first inspection target object is imaged to be enlarged.
Figure 5B:
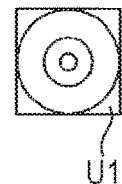
FIG. 5b is a dose distribution image in a case where the first inspection target object is imaged to be enlarged.

FIG. 5a is a schematic diagram of an X-ray fluoroscopic image T1 obtained by imaging the enlarged semiconductor component W1, and FIG. 5b illustrates a cumulative irradiation dose distribution image U1 in an imaging range (a region of S1 on the display image 14a in FIG. 4) on the stage 14 corresponding to an imaging region of the X-ray fluoroscopic image T1. The cumulative irradiation dose distribution image U1 is an image of a dose distribution for the same region as the region in which the X-ray fluoroscopic image T1 is captured, and is enlarged, and thus a dose distribution of the inside of the semiconductor component W1 can be checked from the enlarged image.

Figure 6:
FIG. 6 is a schematic diagram illustrating a state in which the X-ray fluoroscopic image and the dose distribution image in FIG. 5a and FIG. 5b are displayed to be superimposed on each other.

The X-ray fluoroscopic image T1 in FIG. 5a and the dose distribution image U1 in FIG. 5b are displayed in parallel to each other on the display device 24, or, as illustrated in FIG. 6, the X-ray fluoroscopic image T1 and the dose distribution image U1 are displayed to be superimposed on each other in different colors, so as to be observed, and thus the X-ray fluoroscopic image and the dose distribution image can be observed through comparison.

Figure 7:
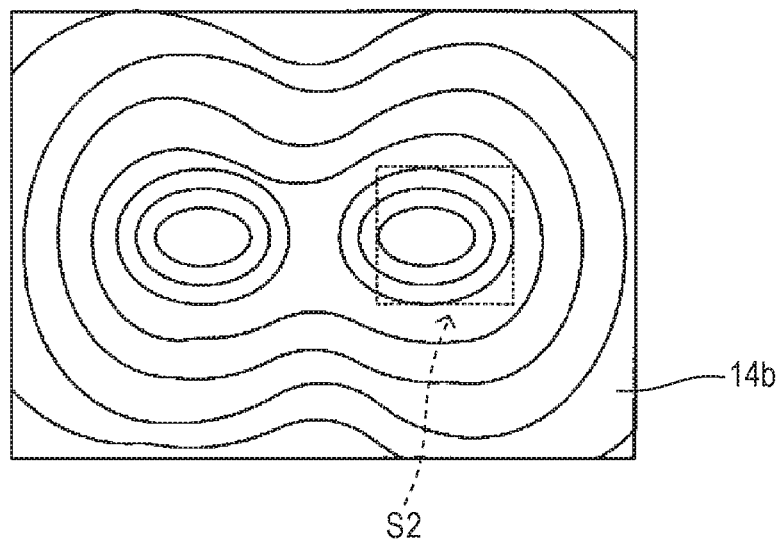
FIG. 7 is a schematic diagram illustrating cumulative irradiation dose distribution data of a second inspection target object.

Thereafter, in order to inspect the semiconductor component W2, the stage 14 is moved such that the semiconductor component W2 is presented on the X-ray optical axis L, a position (magnification factor) thereof in the Z direction is adjusted at the position, observation is performed for the time being, and an image of the cumulative irradiation dose distribution data for the entire stage 14 right after an X-ray fluoroscopic image of the semiconductor component W2 is captured is displayed. FIG. 7 is a schematic diagram illustrating a display image 14b.

The display image 14b of the cumulative irradiation dose distribution data obtained at this time is a dose distribution image in which an irradiation dose applied after the stage is moved is added to the cumulative irradiation dose distribution data in FIG. 4.

Figure 8A:
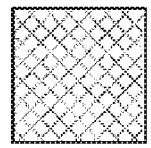
FIG. 8a is a schematic diagram illustrating an X-ray fluoroscopic image in a case where the second inspection target object is imaged to be enlarged.
Figure 8B:
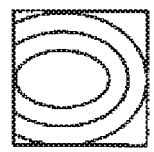
FIG. 8b is a dose distribution image in a case where the second inspection target object is imaged to be enlarged.
Figure 9:
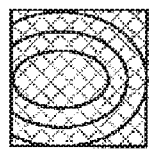
FIG. 9 is a schematic diagram illustrating a state in which the X-ray fluoroscopic image and the irradiation dose distribution image in FIG. 8a and FIG. 8b are displayed to be superimposed on each other.

FIG. 8a is a schematic diagram of an X-ray fluoroscopic image T2 obtained by imaging the enlarged semiconductor component W2, and FIG. 8b illustrates a dose distribution image U2 in an imaging range (a region of S2 on the display image 14b in FIG. 7) on the stage 14 corresponding to an imaging region of the X-ray fluoroscopic image T2. The dose distribution image U2 is an image of a dose distribution for the same region as the region in which the X-ray fluoroscopic image T2 is captured, and is enlarged, and thus a dose distribution of the inside of the semiconductor component W2 can be checked from the enlarged image. As illustrated in FIG. 9, the X-ray fluoroscopic image and the dose distribution image in FIG. 8a and FIG. 8b may be displayed to be superimposed on each other.

In the cumulative irradiation dose distribution images exemplified in FIGS. 4 to 9, for convenience of description, a cumulative irradiation dose distribution is displayed by contour lines, but the distribution is preferably displayed in a color image such as a heat map on the display device 24.

As mentioned above, a cumulative irradiation dose in a region corresponding to a captured X-ray fluoroscopic image can be recognized as a two-dimensional dose distribution image in the unit of a component to be inspected, and thus the influence of X-ray irradiation during X-ray inspection can be visually recognized for each component.

It is possible to check a two-dimensional distribution image of a cumulative irradiation dose in the same region as that of an X-ray fluoroscopic image in accordance with an imaging region in which the X-ray fluoroscopic image is captured without being influenced by enlargement or reduction of the X-ray fluoroscopic image.

The invention claimed is:

1. An X-ray inspection apparatus comprising:
   an X-ray source;
   an X-ray detector that is disposed to face the X-ray source with an inspection space interposed therebetween;
   a stage that is movable to any position in the inspection space by a three-dimensional movement mechanism;
   a dose rate calculation unit that obtains a reference dose rate for at least one position in the inspection space under a tube current and a tube voltage used as references, and stores the reference dose rate as reference dose rate data in advance, and calculates a dose rate at any position in the inspection space as inspection space dose rate data on the basis of the reference dose rate data by setting a tube current and a tube voltage used for inspection of an inspection target object;
   a stage face information storage unit that stores stage face information including a stage reference point defined for the stage and relative position information for defining a range of a stage face;
   an irradiation history monitoring unit that monitors a movement locus of the stage reference point at each time point from starting of X-ray irradiation to ending of X-ray irradiation, and stores the movement locus as irradiation history information;
   a stage face cumulative irradiation dose calculation unit that calculates a cumulative irradiation dose at each position on the stage face of the stage on the basis of the irradiation history information, the stage face information, and the inspection space dose rate data, and stores the cumulative irradiation dose as cumulative irradiation dose distribution data;
   a stage face imaging range calculation unit that calculates stage face imaging range data indicating a range of the stage face imaged by the X-ray detector at a position where an X-ray fluoroscopic image of the inspection target object is captured; and
   a dose distribution image display control unit that extracts cumulative irradiation dose distribution data for a region corresponding to the stage face imaging range data from the cumulative irradiation dose distribution data as imaging range cumulative dose distribution data, and displays an image of the imaging range cumulative dose distribution data on the display device,
   wherein a position of the stage is adjusted such that an observation region of the inspection target object placed on the stage face of the stage is located on an X-ray optical axis connecting the X-ray source to the X-ray detector, and then an X-ray fluoroscopic image of the inspection target object is captured and is displayed on a display device.

2. The X-ray inspection apparatus according to claim 1, wherein the dose rate calculation unit moves the stage under the tube current and the tube voltage used as references, measures a dose per unit time at a plurality of positions in the inspection space with a dosimeter placed on the stage face, stores the dose as a reference dose rate table, and calculates the inspection space dose rate data at any position in the inspection space on the basis of the reference dose rate table.

3. The X-ray inspection apparatus according to claim 1, wherein the dose distribution image display control unit displays the captured X-ray fluoroscopic image of the inspection target object and a two-dimensional distribution image of a cumulative irradiation dose based on the imaging range cumulative dose distribution data corresponding to the X-ray fluoroscopic image to be arranged side by side or to be superimposed on each other.

* * * * *